(12) United States Patent
Nakashima et al.

(10) Patent No.: US 7,827,849 B2
(45) Date of Patent: Nov. 9, 2010

(54) GAS SENSOR

(75) Inventors: Takashi Nakashima, Aichi (JP); Yuichi Yamada, Aichi (JP); Masashi Ando, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 219 days.

(21) Appl. No.: 11/928,505

(22) Filed: Oct. 30, 2007

(65) Prior Publication Data

US 2008/0105037 A1 May 8, 2008

Related U.S. Application Data

(60) Provisional application No. 60/946,906, filed on Jun. 28, 2007.

(30) Foreign Application Priority Data

Nov. 2, 2006 (JP) .............................. 2006-298526

(51) Int. Cl.
*G01N 7/00* (2006.01)
(52) U.S. Cl. ...................... 73/23.31; 204/424; 73/23.2
(58) Field of Classification Search .................. 73/23.1, 73/23.2, 31.05, 23.31, 23.32; 204/424, 428
See application file for complete search history.

(56) References Cited

U.S. PATENT DOCUMENTS

| 5,012,670 | A | * | 5/1991 | Kato et al. ................. 73/31.05 |
| 6,279,376 | B1 | * | 8/2001 | Yamada et al. ............... 73/23.2 |
| 6,682,639 | B2 | * | 1/2004 | Atsumi et al. ............... 204/428 |
| 6,726,819 | B2 | * | 4/2004 | Atsumi et al. ............... 204/428 |
| 7,390,385 | B2 | * | 6/2008 | Ikoma et al. ................. 204/428 |
| 7,461,538 | B2 | * | 12/2008 | Matsuo et al. ............. 73/23.31 |
| 7,559,229 | B2 | * | 7/2009 | Yamada ..................... 73/31.05 |
| 2003/0121782 | A1 | * | 7/2003 | Atsumi et al. ............... 204/424 |
| 2003/0146093 | A1 | * | 8/2003 | Akiyama et al. ............ 204/424 |
| 2004/0159547 | A1 | * | 8/2004 | Haraguchi et al. .......... 204/424 |
| 2005/0241937 | A1 | | 11/2005 | Shichida et al. |
| 2007/0251823 | A1 | | 11/2007 | Yamada |

FOREIGN PATENT DOCUMENTS

| JP | 2004-125702 | 4/2004 |
| WO | WO 2005/017515 A1 | 2/2005 |

\* cited by examiner

*Primary Examiner*—Lisa M Caputo
*Assistant Examiner*—Punam Roy
(74) *Attorney, Agent, or Firm*—Sughrue Mion, PLLC (57) ABSTRACT

A gas sensor (1) including a protector (100) for protecting a detection portion (11) of a sensor element (10). The protector (100) has an inner protector (120) and an outer protector (110). A diameter r of an exhaust hole (160) formed in the inner protector (120) and an axial distance h between a front end 10*a* of the sensor element 10 and the exhaust hole (160) satisfy a relation $r \leq 2h/15 + \frac{1}{3}$.

9 Claims, 7 Drawing Sheets

GAS SENSOR

CROSS-REFERENCE TO RELATED APPLICATION

This application claims benefit of U.S. Provisional Application No. 60/946,906 filed Jun. 28, 2007, incorporated herein by reference.

BACKGROUND OF THE INVENTION

1. Field of the Invention

The present invention relates to a gas sensor having a protector for protecting a detection element exposed to exhaust gas from adhesion of water.

2. Description of the Related Art

Conventionally, a gas sensor is known having a detection element which generates an electromotive force of a magnitude corresponding to the concentration of a specific gas component; for example, $NO_x$ (nitrogen oxides) or oxygen, contained in exhaust gas of an automobile or the like or whose resistance varies with concentration of the gas component. The gas sensor is attached, for use, to an exhaust gas pipe of an automobile or the like. Because the detection element is exposed to a high temperature exhaust gas, subjecting the detection element to thermal shock caused by adhesion of water contained in the exhaust gas may crack or break the detection element. In order to address the above-noted problem, the gas sensor is fit with a protector for covering the detection element, thereby protecting the detection element from adhesion of water (refer to, for example, Patent Document 1).

The protector of the gas sensor of Patent Document 1 has a dual structure consisting of an outer protector and an inner protector. A front-end circumferential portion (a lower circumferential portion as viewed when the gas sensor is attached) of the outer protector has outer introduction holes for introducing exhaust gas toward a clearance between the outer protector and the inner protector (hereinafter, also referred to as the "gas separation chamber"). Guide portions are provided at the respective outer introduction holes of the outer protector so as to cause exhaust gas introduced into the gas separation chamber to swirl around the outer circumferential surface of the inner protector. Inertial force associated with the swirl separates a gas component from water which is heavy relative to the gas component. A rear-end circumferential portion (an upper circumferential portion as viewed when the gas sensor is attached) of the inner protector has inner introduction holes for introducing the gas component, which is separated in the gas separation chamber, into the interior of the inner protector.

The inner protector of the gas sensor of Patent Document 1 has a bottom portion projecting from the front end of the outer protector and has an exhaust hole formed in the bottom portion. Thus, a gas component of exhaust gas which is introduced into the inner protector can be exhausted from the exhaust hole.

[Patent Document 1] Japanese Patent Application Laid-Open (kokai) No. 2004-109125, which corresponds to US 2005/241937A1.

3. Problems to be Solved by the Invention

However, in the gas sensor of Patent Document 1, the exhaust hole of the inner protector has a size which ensures exhaust-gas exhaustibility. Thus, in some cases, a water droplet or the like can enter the inner protector through the exhaust hole. Since a front end portion of the detection element is directly visible from the outside, a water droplet which enters through the exhaust hole may adhere to the detection element. If the detection element is subjected to thermal shock caused by such a water droplet, the detection element may crack or break.

SUMMARY OF THE INVENTION

The present invention has been achieved for solving the above problems, and an object thereof is to provide a gas sensor having a protector which can effectively protect a detection element from adhesion of water while maintaining good gas exhaustibility.

The above object of the invention has been achieved by providing a gas sensor which comprises a detecting element, extending in an axial direction of the gas sensor, and having a detecting portion which is provided at a front end portion of the detecting element and adapted to detect a specific gas component contained in a gas-to-be-measured; a housing which encloses the detection element with the detection portion of the detection element projecting from a front end of the housing; an inner protector accommodating the detection portion of the detection element therein, the inner protector including a bottom portion having an exhaust hole, a circumferential portion having inner introduction holes for introducing the gas-to-be-measured into the interior of the inner protector, and a rear end portion fixed to a front end portion of the housing; and an outer protector enclosing the inner protector with a clearance present between the inner protector and the outer protector, the outer protector including a circumferential portion having outer introduction holes for introducing the gas-to-be-measured into the clearance, and a rear end portion fixed to the front end portion of the housing, wherein an axial distance h (mm) between a front end of the detection element and the exhaust hole and a diameter r (mm) of the exhaust hole satisfy a relation $r \leq 2h/15 + 1/3$, where $0 < h$ and $0 < r$.

In a preferred embodiment of the invention, the diameter r of the exhaust hole is equal to or greater than 0.5 mm.

Furthermore, in yet another preferred embodiment, the axial distance h between the front end of the detection element and the exhaust hole is equal to or less than 15 mm.

EFFECT OF THE INVENTION

In the gas sensor of the invention, the axial distance h between the front end of the detection element and the exhaust hole and the diameter r of the exhaust hole of the inner protector satisfy the relation $r \leq 2h/15 + 1/3$, thereby restraining adhesion, to the detection element, of a water droplet which has entered through the exhaust hole, and in turn restraining the occurrence of cracking or breakage of the detection element, while ensuring exhaust-gas exhaustibility of the exhaust hole of the inner protector.

When the axial distance h (mm) between the front end of the detection element and the exhaust hole and the diameter r (mm) of the exhaust hole satisfy the relation $2h/15 + 1/3 < r$, the diameter of the exhaust hole becomes excessively large. As a result, a water droplet which enters through the exhaust hole may adhere to the detection element, and a resultant thermal shock imposed on the detection element may crack or break the detection element.

Preferably, the diameter r of the exhaust hole is equal to or greater than 0.5 mm. This can further ensure exhaust-gas exhaustibility of the exhaust hole of the inner protector. If the diameter r of the exhaust hole is less than 0.5 mm, the exhaust hole may be clogged with carbon or the like contained in exhaust gas. As a result, exhaustibility may suffer. Also, an exhaust hole having a diameter r of less than 0.5 mm is difficult to form.

The greater the axial distance h (mm) between the front end of the detection element and the exhaust hole, the greater the effect of restraining adhesion, to the detection element, of a water droplet which has entered through the exhaust hole. Consequently, the occurrence of cracking or breakage of the detection element can further be restrained. However, this prevents easy contact between the detection portion of the detection element and a gas component of exhaust gas introduced into the inner protector, such that gas detection accuracy may suffer. Thus, the detection portion of the detection element must be disposed within the inner protector to allow contact between the detection portion of the detection element and a gas component of exhaust gas introduced into the inner protector.

Preferably, the axial distance h (mm) between the front end of the detection element and the exhaust hole is equal to or less than 15 mm. This ensures sufficient contact between the detection portion of the detection element and a gas component of exhaust gas introduced into the inner protector. If the axial distance h (mm) between the front end of the detection element and the exhaust hole is greater than 15 mm, contact between the detection portion of the detection element and a gas component of exhaust gas introduced into the inner protector may become more difficult. Also, the inner protector becomes excessively long and may not fit into an exhaust pipe.

No particular limitation is imposed on the outer introduction holes of the outer protector, so long as the outer introduction holes are located frontward of the inner introduction holes of the inner protector. Specifically, the front ends of the outer introduction holes may be located frontward of the front ends of the inner introduction holes. Preferably, in order to effectively protect the detection element from adhesion of water, the rear ends of the outer introduction holes are located frontward of the front ends of the inner introduction holes. Furthermore, the number of the outer introduction holes and the number of the inner introduction holes may be one. However, in order to eliminate the need to consider orientation, position, etc., of the gas sensor when the gas sensor is attached to an exhaust pipe, preferably, a plurality of outer introduction holes and a plurality of inner introduction holes are provided. Also, preferably, the outer introduction holes and the inner introduction holes are respectively formed at equal circumferential intervals.

DESCRIPTION OF REFERENCE NUMERALS

Reference numerals used to identify various structural features in the drawings include the following:
1: gas sensor
10: sensor element
11: detection portion
15: protection layer
50: metallic housing
56: front-end engaging-portion
110: outer protector
113, 113': outer taper portion
115: outer introduction hole
119: gas separation chamber (clearance)
120: inner protector
124: inner taper portion
121: rear end portion
130, 140: inner introduction hole
160: exhaust hole
250: drain outlet

DETAILED DESCRIPTION OF THE PREFERRED EMBODIMENTS

A gas sensor according to an embodiment of the present invention will next be described with reference to the drawings. However, the present invention should not be construed as being limited thereto.

Figure 1:
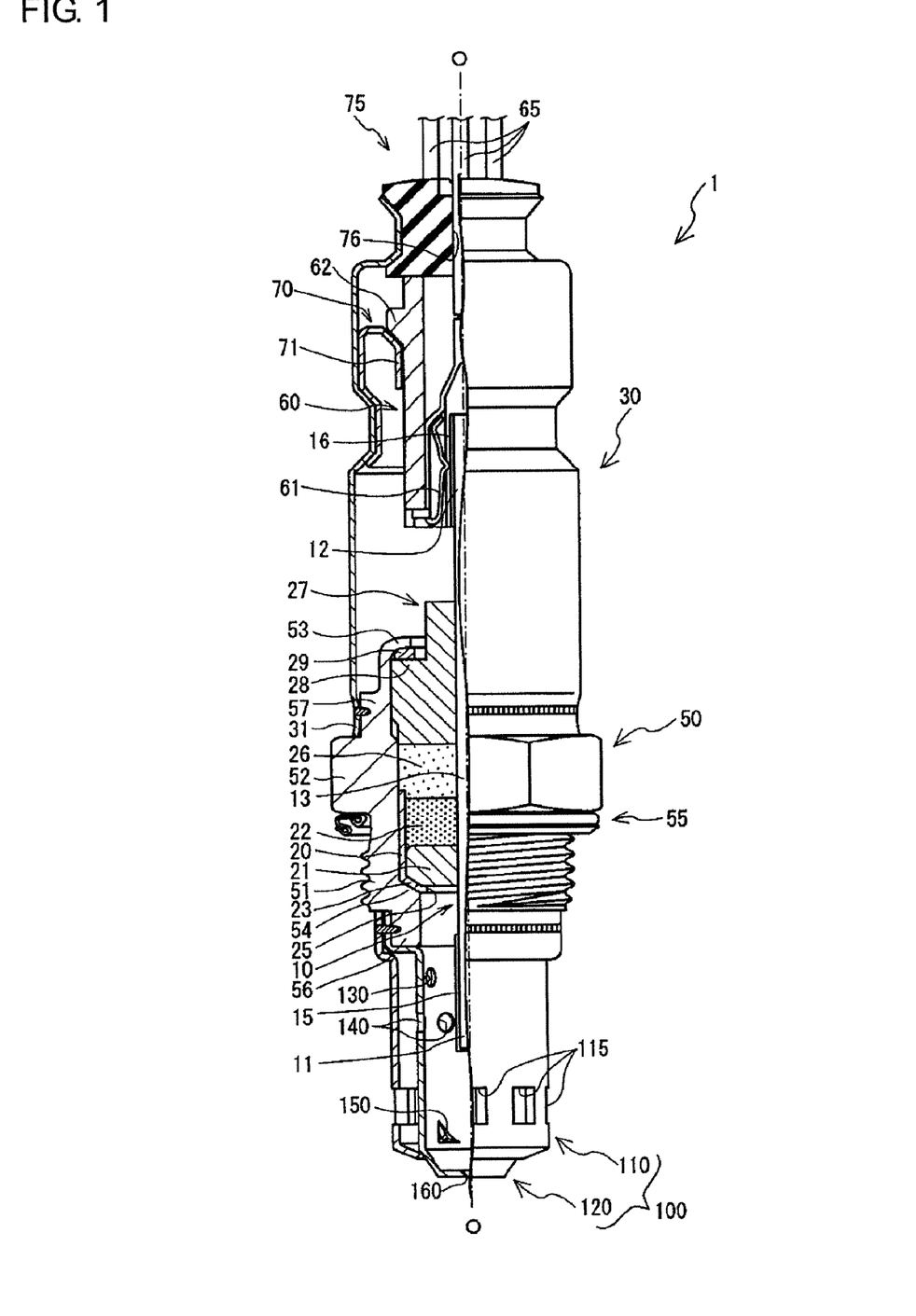
FIG. 1 is a partial sectional view of a gas sensor 1.
Figure 2:
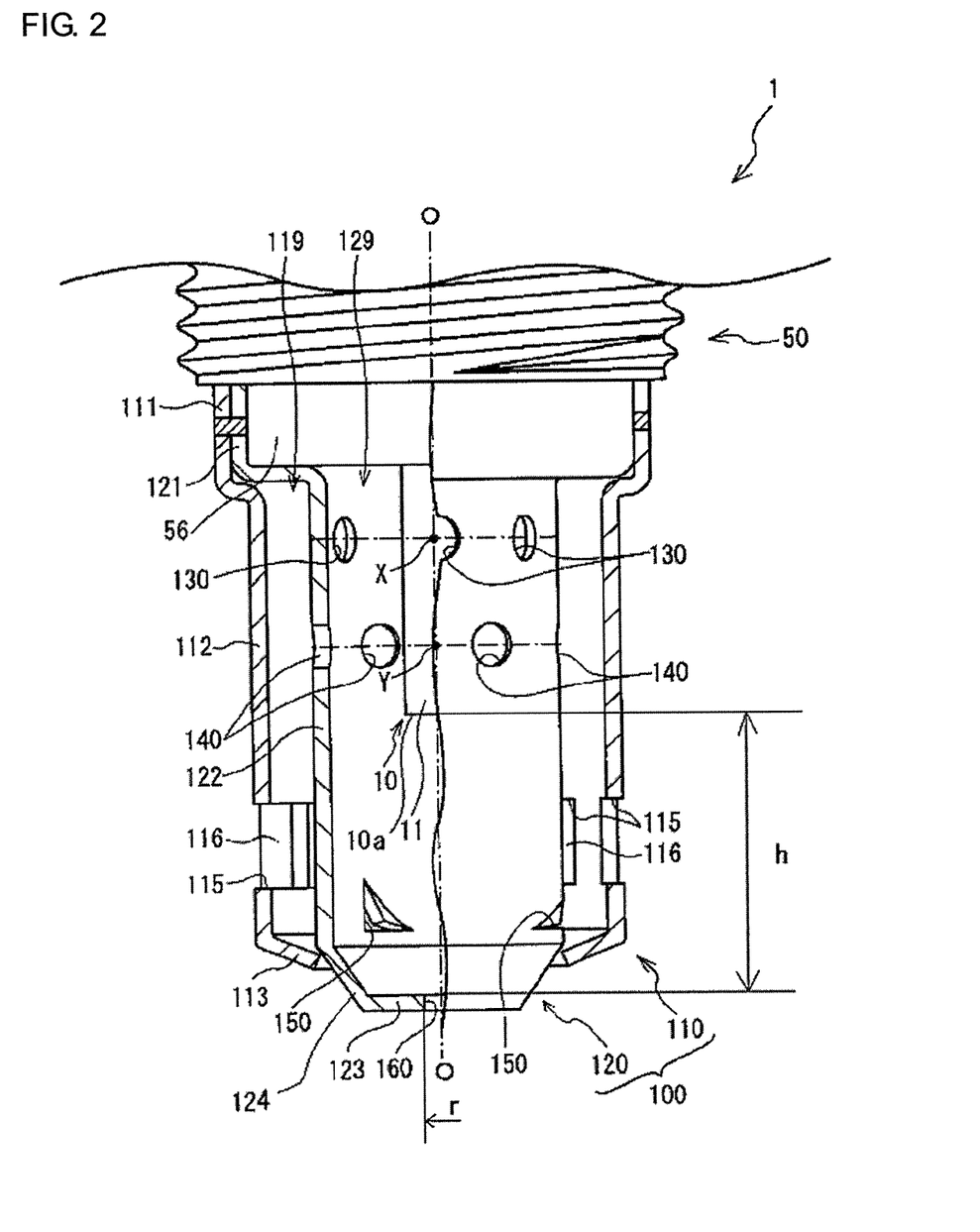
FIG. 2 is a partial sectional view on an enlarged scale of a front end portion of the gas sensor 1.

First, the structure of a gas sensor 1 will be described, by way of example, with reference to FIGS. 1 and 2. FIG. 1 is a partial sectional view of the gas sensor 1. FIG. 2 is a partial sectional view on an enlarged scale of a front end portion of the gas sensor 1. Notably, in FIGS. 1 and 2, the direction of an axis O of the gas sensor 1 (represented by a dot-dash line) coincides with the vertical direction. In the following description, a side toward a detection portion 11 of a sensor element 10 held in the interior of the gas sensor 1 is referred to as a front-end side of the gas sensor 1, and a side toward a rear end portion 12 is referred to as a rear-end side of the gas sensor 1.

The gas sensor 1 shown in FIG. 1 is attached to an exhaust pipe of an automobile (not shown). The detection portion 11 of the sensor element 10 held in the interior of the gas sensor 1 is exposed to exhaust gas which flows through the exhaust pipe, e.g., for detecting the air/fuel ratio of the exhaust gas from the oxygen concentration of the exhaust gas; i.e., the gas sensor 1 is a so-called full-range air/fuel ratio sensor.

As well known to those skilled in this field of art, the sensor element 10 assumes the form of a strip extending in the direction of the axis O and is a generally rectangular columnar laminate in which a gas-detection element for detecting an oxygen concentration and a heater element for promptly activating the gas-detection element through application of heat are laminated. The gas-detection element is composed of a solid electrolyte body (not shown) which predominantly contains zirconia, and detection electrodes (not shown) which predominantly contain platinum. The detection electrodes are disposed at the detection portion 11 located at the front end of the sensor element 10. In order to protect the detection electrodes from poisoning by exhaust gas, the detection portion 11 of the sensor element 10 is covered with a protection layer 15. Preferably, the protection layer has a thickness of 150 μm to 250 μm. In the present embodiment, the thickness is about 200 μm. The rear end portion 12 of the sensor element 10 has five electrode pads 16 (one of which is shown in FIG. 1) for allowing external connection with electrodes extending from the gas-detection element and from the heater element. Notably, in the description of the present embodiment, the sensor element 10 includes the "detection element" in the present invention. However, strictly speaking, the detection element does not necessarily include a heater element; thus, the gas-detection element corresponds to the "detection element" of the present invention.

A closed-bottomed tubular metal cup 20 is disposed slightly frontward of the axial center of a trunk portion 13 of the sensor element 10 in such manner that the sensor element 10 is inserted through the interior of the metal cup 20 with the detection portion 11 projecting from an opening 25 formed in a bottom of the metal cup 20. The metal cup 20 is a member for holding the sensor element 10 in a metallic housing 50. A front-end peripheral-portion 23 located at a peripheral portion of the bottom of the metal cup 20 is tapered toward a tubular wall portion of the metal cup 20. The metal cup 20 contains a ceramic holder 21 made of alumina and a talc ring 22 formed by compacting a talc powder, in such a manner that the sensor element 10 is inserted through the ceramic holder 21 and through the talc ring 22. The talc ring 22 is crushed within the metal cup 20 so as to tightly fill an associated space, thereby holding the sensor element 10 in position in the metal cup 20.

An assembly of the metal cup 20 and the sensor element 10 is circumferentially enclosed and held by the tubular metallic housing 50. The metallic housing 50 is adapted to fixedly attach the gas sensor 1 to an exhaust pipe of an automobile (not shown). The metallic housing 50 is formed from a low-carbon steel such as SUS430 and has an externally threaded portion 51 which is formed on an outer circumferential surface of the metallic housing 50 and located on a side toward the front end of the metallic housing 50. The metallic housing 50 has a front-end engaging-portion 56 which is located frontward of the externally threaded portion 51 and engaged with a protector 100, which will be described below. The metallic housing 50 also has a tool engagement portion 52 which is formed at an axially central portion of an outer circumferential surface of the metallic housing 50 and with which a mounting tool is engaged. In order to prevent leakage of gas when the gas sensor 1 is attached to the exhaust pipe, a gasket 55 is fitted to a portion of the metallic housing 50 between the front end face of the tool engagement portion 52 and the rear end of the externally threaded portion 51. The metallic housing 50 further has a rear-end engaging-portion 57 which is located rearward of the tool engagement portion 52 and with which a sheath 30 to be described below is engaged, and a crimp portion 53 which is located rearward of the rear-end engaging-portion 57 and adapted to crimp-hold the sensor element 10 in the metallic housing 50. Notably, the metallic housing 50 corresponds to the "housing" in the present invention.

The metallic housing 50 has a stepped portion 54 on its inner circumferential surface at a position substantially corresponding to the externally threaded portion 51. The front-end peripheral-portion 23 of the metal cup 20 which holds the sensor element 10 is engaged with the stepped portion 54. Furthermore, a talc ring 26 is placed in the metallic housing 50 along the inner circumference of the metallic housing 50 from the rear side of the metal cup 20 in such a state that the sensor element 10 is inserted through the talc ring 26. A tubular sleeve 27 is fitted into the metallic housing 50 so as to press the talc ring 26 from the rear side of the talc ring 26. The sleeve 27 has a step-like shoulder portion 28 formed on the outer circumferential surface of a rear end portion of the sleeve 27. An annular crimp packing 29 is disposed on the shoulder portion 28. In this arrangement, the crimp portion 53 of the metallic housing 50 is crimped so as to press the shoulder portion 28 of the sleeve 27 frontward via the crimp packing 29. The talc ring 26 pressed by the sleeve 27 is crushed within the metallic housing 50, thereby tightly filling an associated space. By means of the talc ring 26 and the talc ring 22, which is previously placed in the metal cup 20, the metal cup 20 and the sensor element 10 is held in position in the metallic housing 50. Airtightness within the metallic housing 50 is maintained by means of the crimp packing 29 intervening between the crimp portion 53 and the shoulder portion 28 of the sleeve 27, thereby preventing outflow of combustion gas.

The rear end portion 12 of the sensor element 10 projects rearward beyond the rear end (crimp portion 53) of the metallic housing 50. The rear end portion 12 is covered with a tubular separator 60 formed from an insulating ceramic. The separator 60 internally holds the five electrode pads 16 formed on the rear end portion 12 of the sensor element 10 and five connection terminals 61 (one of which is shown in FIG. 1), which are electrically connected to the respective electrode pads 16. Also, the separator 60 protectively accommodates connections between the connection terminals 61 and corresponding five lead wires 65 (three of which are shown in FIG. 1), which extend to the exterior of the gas sensor 1.

The tubular sheath 30 is disposed so as to circumferentially enclose the rear end portion 12 of the sensor element 10 to which the separator 60 is fitted. The sheath 30 is made of stainless steel (e.g., SUS304). A front open end 31 of the sheath 30 is engaged with the outer circumference of the rear-end engaging-portion 57 of the metallic housing 50. The open end 31 is crimped radially inward, and laser welding is performed on the open end 31 along the outer circumference of the open end 31, whereby the open end 31 is joined to the rear-end engaging-portion 57. The sheath 30 and the metallic housing 50 are thus united.

A tubular metal holder 70 is disposed in the clearance between the sheath 30 and the separator 60. The metal holder 70 has a support portion 71, which is formed by inwardly bending a rear end of the metal holder 70. The separator 60 is inserted through the metal holder 70 such that a flange portion 62 formed on the outer circumference of a rear end portion of the separator 60 is engaged with the support portion 71, whereby the separator 60 is supported by the support portion 71. In this arrangement, a portion of the sheath 30 where the metal holder 70 is disposed is crimped radially inward, whereby the metal holder 70 which supports the separator 60 is fixed to the sheath 30.

A grommet 75 made of fluorine-containing rubber is fitted into a rear end opening of the sheath 30. The grommet 75 has five insertion holes 76 (one of which is shown in FIG. 1). The five lead wires 65 extending outwardly from the separator 60 are airtightly inserted through the respective insertion holes 76. In this arrangement, a portion of the sheath 30 which corresponds to the grommet 75 is crimped radially inward, whereby the grommet 75 is fixed to the rear end of the sheath 30 while pressing the separator 60 frontward.

While the sensor element 10 is held in the metallic housing 50, the detection portion 11 of the sensor element 10 projects from a front end portion (front-end engaging-portion 56) of the metallic housing 50. The protector 100 is fitted to and laser-welded to the front-end engaging-portion 56 for the purpose of protecting the detection portion 11 of the sensor element 10 from breakage or the like which could otherwise result from contamination with deposits (poisonous adhering substances such as fuel ash and oil components) contained in exhaust gas and adhesion of water. The protector 100 has a dual-structure consisting of a closed-bottomed tubular inner protector 120 having a plurality of holes formed in its side wall, and an outer protector 110, which assumes a tubular form so as to circumferentially enclose the inner protector 120 with a clearance (a gas separation chamber 119 (see FIG. 2)) formed between an outer circumferential surface of the inner protector 120 and an inner circumferential surface of the outer protector 110 and which has a plurality of holes formed in its side wall.

As shown in FIG. 2, the outside diameter of the inner protector 120 is smaller than the outside diameter of the front-end engaging-portion 56 of the metallic housing 50. A rear end portion 121 associated with an open end (rear end) of the inner protector 120 is expanded in diameter so as to be engaged with the front-end engaging-portion 56. A side wall 122 of the inner protector 120 has a plurality of (six in the present embodiment) inner introduction holes 130 which are arranged circumferentially at a position X located toward the rear end portion 121 with respect to the direction of the axis O. The side wall 122 also has a plurality of (six in the present embodiment) inner introduction holes 140 which are arranged circumferentially and located at a position Y located frontward of the position X with respect to the direction of the axis O. The inner introduction holes 130 and 140 are adapted to introduce mainly a gas component of exhaust gas, which is introduced into the clearance (the gas separation chamber 119) formed between the outer protector 110 and the inner protector 120 through outer introduction holes 115 of the outer protector 110 described below, and, into the interior of the inner protector 120; i.e., into a detection chamber 129 to which the detection portion 11 of the sensor element 10 is exposed.

A front end portion of the side wall 122 of the inner protector 120 has drain holes 150 which wedgewise open into the interior of the inner protector 120 and which are arranged at a plurality of (three in the present embodiment) circumferential positions. A bottom wall 123 of the inner protector 120 has an exhaust hole 160. Furthermore, an inner taper portion 124 is formed between the side wall 122 and the bottom wall 123.

Next, as in the case of the inner protector 120, a rear end portion 111 of the outer protector 110 associated with an open end of the outer protector 110 has an expanded diameter. The rear end portion 111 is engaged with the rear end portion 121 of the inner protector 120. Laser welding is performed along the entire circumference of the rear end portion 111 of the outer protector 110 so as to fix the rear end portion 111 of the outer protector 110 and the rear end portion 121 of the inner protector 120 to the front-end engaging-portion 56. An outer taper portion 113 located at the front end of the outer protector 110 is bent inward toward the inner taper portion 124 of the inner protector 120, thereby exposing the bottom wall 123 of the inner protector 120 from the outer protector 110. This closes the clearance formed between the outer circumferential surface of the inner protector 120 and the inner circumferential surface of the outer protector 110 at the front end of the clearance, thereby forming the gas separation chamber 119. Since the inner protector 120 and the outer protector 110 have the inner taper portion 124 and the outer taper portion 113, respectively, exhaust of gas and water droplets through the exhaust hole 160 is accelerated.

A front end portion of a side wall 112 of the outer protector 110 has a plurality of (eight in the present embodiment) outer introduction holes 115 which are arranged circumferentially at a position located frontward of the above-mentioned position Y with respect to the direction of the axis O and which are adapted to establish atmospheric communication between the exterior and the interior of the outer protector 110. Each of the outer introduction holes 115 has a guide portion 116 which extends inward. The guide portions 116 cause exhaust gas, which is externally introduced into the gas separation chamber 119 through the outer introduction holes 115, to swirl around the outer circumferential surface of the side wall 122 of the inner protector 120.

Figure 3:
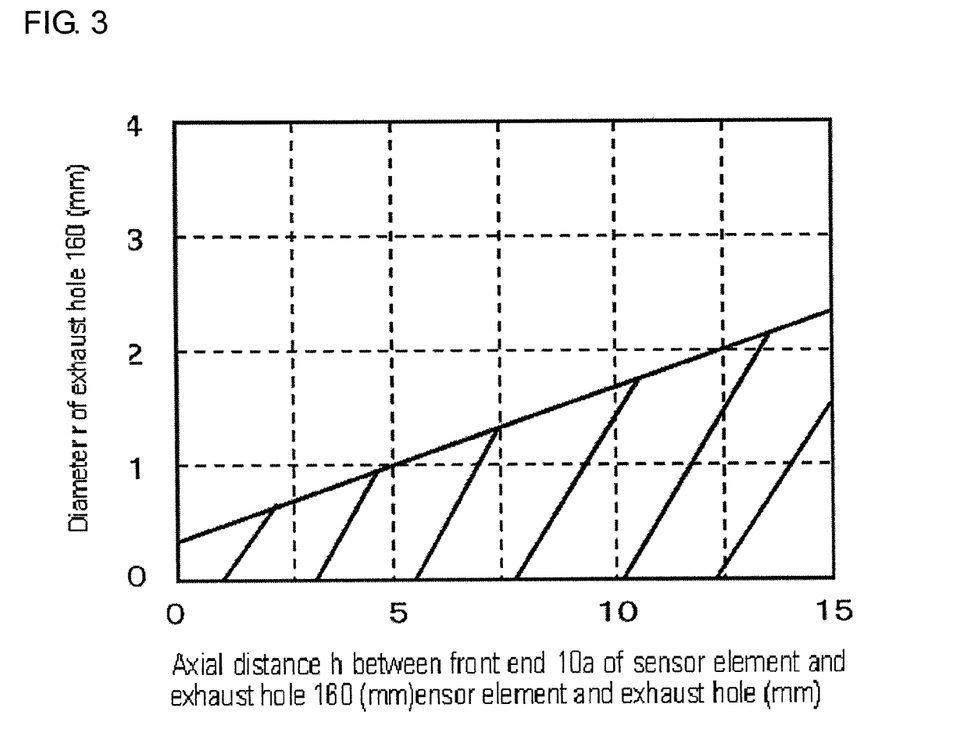
FIG. 3 is a diagram showing a region of the present invention satisfying the relationship $r \leq 2h/15 + 1/3$, where r is the diameter of an exhaust hole 160 and h is an axial distance between a front end 10a of a sensor element 10 and the exhaust hole 160.

In the thus-configured gas sensor 1, in order to protect the sensor element 10 exposed to the detection chamber 129 (the interior of the inner protector 120) from adhesion of water, a requirement is imposed on the diameter r of the exhaust hole 160 of the inner protector 120 and the axial distance h between a front end 10a of the sensor element 10 and the exhaust hole 160. Specifically, the requirement is expressed by $r \leq 2h/15 + \frac{1}{3}$, as shown in the hatched area of FIG. 3. This restrains adhesion, to the sensor element 10, of a water droplet which has entered through the exhaust hole 160, and in turn restrains the occurrence of cracking or breakage of the sensor element 10, while ensuring exhaust-gas exhaustibility of the exhaust hole 160 of the inner protector 120.

Preferably, the diameter r (mm) of the exhaust hole 160 is equal to or greater than 0.5 mm. This can further ensure exhaust-gas exhaustibility of the exhaust hole 160 of the inner protector 120.

Preferably, the axial distance h (mm) between the front end of the sensor element 10 and the exhaust hole 160 is equal to or less than 15 mm. This ensures sufficient contact between the detection portion of the sensor element 10 and a gas component of exhaust gas introduced into the inner protector 120.

EXAMPLES

In order to verify the effect of the present invention, a water adhesion test was carried out on the gas sensor 1.

In the following Examples 1 to 3, measurement was carried out under the same conditions. Specifically, the gas sensor 1 was attached to an exhaust pipe having a diameter of about 50 mm. The gas sensor 1 was attached so as to be inclined toward the upstream side at an angle of 30°. Water was sprayed from the upstream side, and the maximum diameter (mm) of a water droplet adhering to the sensor element 10 was measured. Water was sprayed under the following conditions. Water flow rate: 12 m/s; atmosphere: room temperature (25° C.); water pressure: 0.2 MPa; and exhaust pressure: atmospheric pressure. A spray pattern was turned ON and OFF three times at an interval of 5 seconds.

Example 1

First, the diameter of the exhaust hole 160 of the inner protector 120 was fixed to 1 mm. While the axial distance h between the front end of the sensor element 10 and the exhaust hole 160 was varied, the maximum diameter (mm) of a water droplet adhering to the sensor element 10 was measured. The results are shown in the diagram of FIG. 4.

Figure 4:
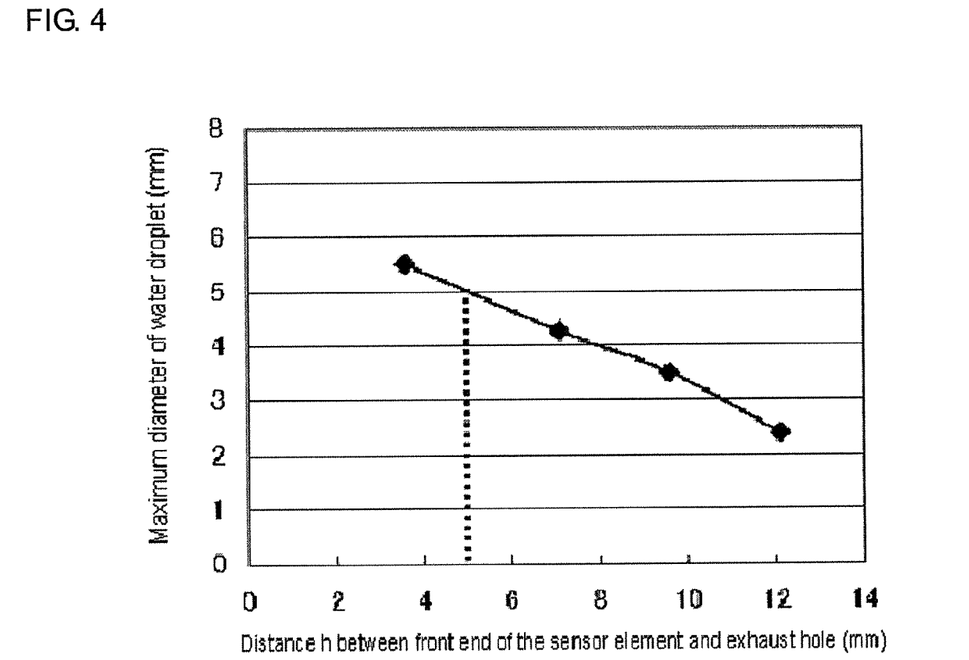
FIG. 4 is a diagram of the results of Example 1, showing maximum diameter (mm) of a water droplet adhering to the sensor element 10 as a function of distance h (mm) between the front end 10a of the sensor element 10 and the exhaust hole 160.

As shown in FIG. 4, the longer the axial distance h between the front end of the sensor element 10 and the exhaust hole 160, the smaller the maximum diameter of a water droplet adhering to the sensor element 10. When the axial distance h between the front end of the sensor element 10 and the exhaust hole 160 was 5 mm, the maximum diameter of a water droplet adhering to the sensor element 10 was 5 mm. An adhering water droplet having a maximum diameter of 5 mm or greater generally causes cracking or the like of the gas sensor element 10. That is, when the axial distance h between the front end of the sensor element 10 and the exhaust hole 160 is 5 mm or greater, the occurrence of cracking or the like of the gas sensor element 10 can be restrained.

Example 2

Next, the axial distance h between the front end of the sensor element 10 and the exhaust hole 160 was fixed to 12.5 mm. While the diameter r of the exhaust hole 160 was varied, the maximum diameter (mm) of a water droplet adhering to the sensor element 10 was measured. The results are shown in FIG. 5.

Figure 5:
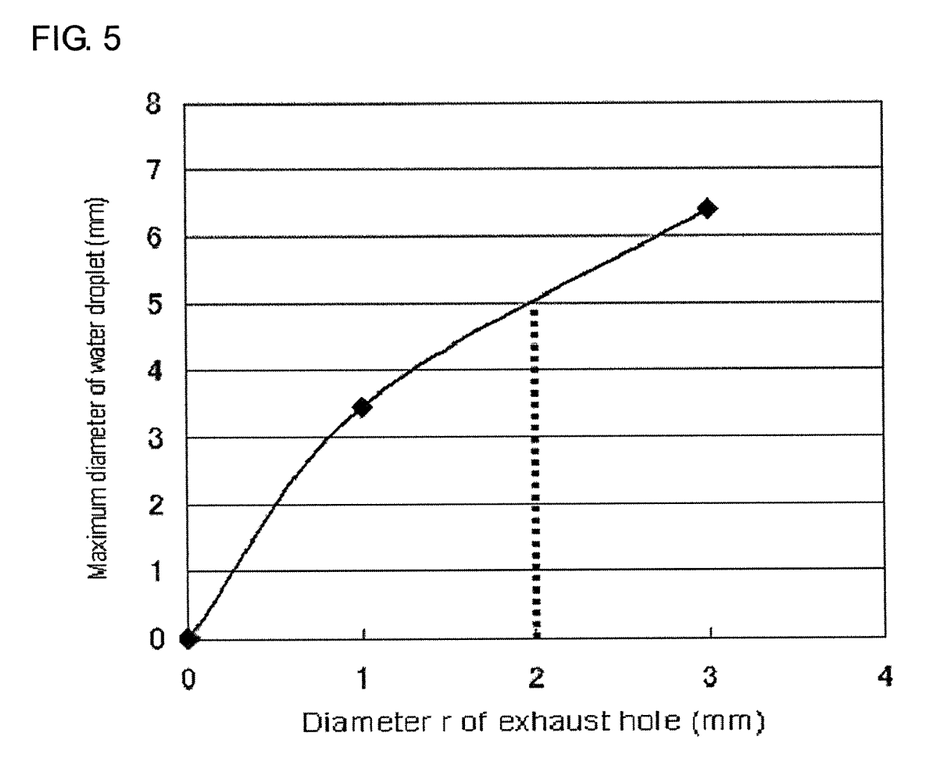
FIG. 5 is a diagram of the results of Example 2, showing maximum diameter (mm) of a water droplet adhering to the sensor element 10 as a function of the diameter r (mm) of the exhaust hole 160, where the axial distance h was fixed to 12.5 mm.

As shown in FIG. 5, the greater the diameter r of the exhaust hole 160, the greater the maximum diameter of a water droplet adhering to the sensor element 10. When the diameter r of the exhaust hole 160 was 2 mm, the maximum diameter of a water droplet adhering to the sensor element 10 was 5 mm. That is, when the diameter r of the exhaust hole 160 is 2 mm or less, the occurrence of cracking or the like of the gas sensor element 10 can be restrained.

Example 3

Next, the axial distance h between the front end of the sensor element 10 and the exhaust hole 160 was fixed to 10 mm. While the diameter r of the exhaust hole 160 was varied, the maximum diameter (mm) of a water droplet adhering to the sensor element 10 was measured. The results are shown in FIG. 6.

Figure 6:
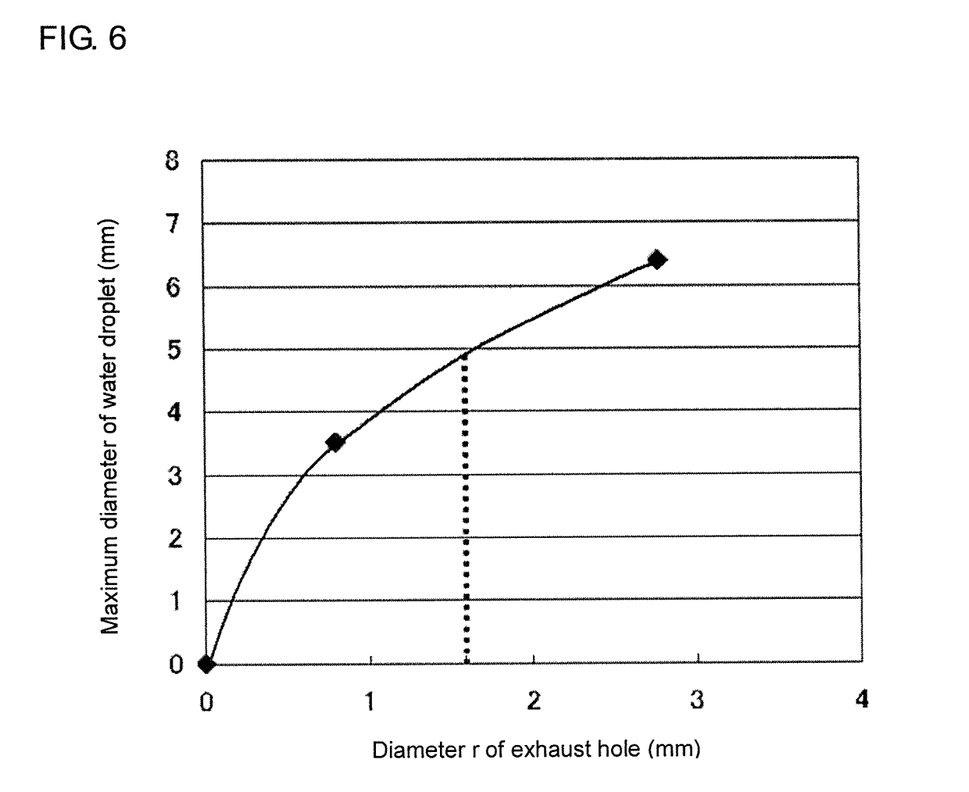
FIG. 6 is a diagram of the results of Example 3, showing maximum diameter (mm) of a water droplet adhering to the sensor element 10 as a function of the diameter r (mm) of the exhaust hole 160, where the axial distance h was fixed to 10 mm.

As shown in FIG. 6, the greater the diameter r of the exhaust hole 160, the greater the maximum diameter of a water droplet adhering to a sensor element 10. When the diameter r of the exhaust hole 160 was 1.65 mm, the maximum diameter of a water droplet was 5 mm. That is, when the diameter r of the exhaust hole 160 is 1.65 mm or less, the occurrence of cracking or the like of the gas sensor element 10 can be restrained.

Thus, by satisfying the dimensional relation $r \leqq 2h/15 + 1/3$, adhesion, to the sensor element 10, of a water droplet which has entered through the exhaust hole 160 can be restrained, thereby restraining the occurrence of cracking or breakage of the sensor element 10.

The present invention is not limited to the above-described embodiment, but may be embodied in various other forms. For example, the inner introduction holes 130 and 140 are formed in the side wall 122 so as to be arranged circumferentially and located at the different positions X and Y, respectively, with respect to the direction of the axis O; i.e., the inner introduction holes 130 and 140 are provided in two levels with respect to the direction of the axis O. However, the inner introduction holes may be provided at three or more different positions; i.e., in three or more levels, with respect to the direction of the axis O.

The shape of the openings of the inner introduction holes 130 and 140 and the exhaust hole 160 is not limited to a circular shape, but may be configured as an ellipse, polygon, or slit. In this case, preferably, the openings assume a shape so as not to allow passage of a sphere having a diameter greater than 2.0 mm. In view of durability of a jig used in manufacture, and the like, a circular shape is desirable. As in the above-described embodiment, in the case where the inner introduction holes 130 and 140 are arranged internally of the outer protector 110, and where the exhaust hole 160 is located externally of the outer protector 110, preferably, the diameter r of the exhaust hole is made smaller than the diameter R of the inner introduction holes 130 and 140. By imparting a smaller diameter to the exhaust hole 160, through which a water droplet is more likely to enter, adhesion of a water droplet to the detection element can be effectively prevented.

Figure 7:
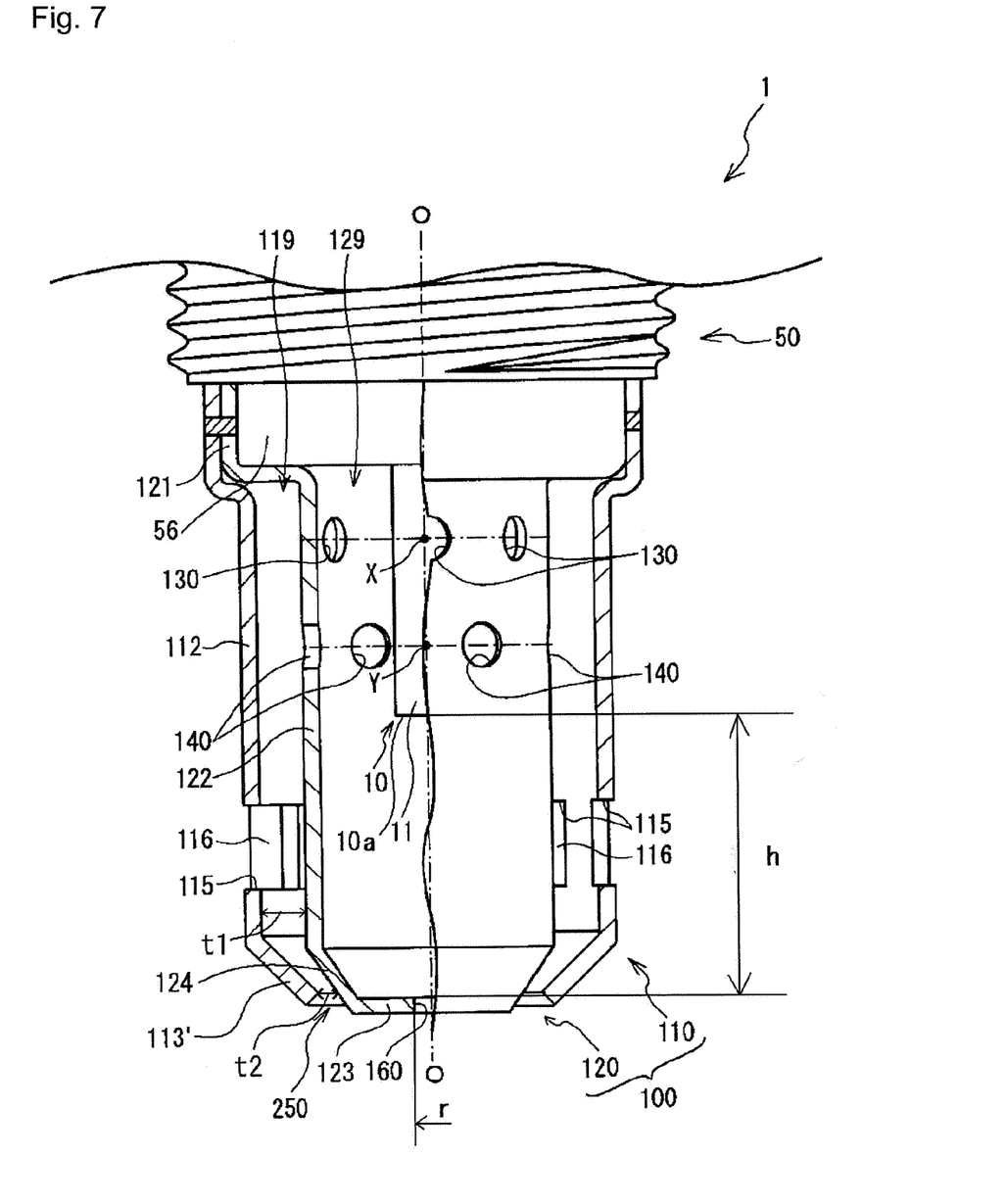
FIG. 7 is a partial sectional view of an enlarged scale of a front end portion of a gas sensor according to a modified embodiment.

The front end of the outer taper portion 113 is in contact with the inner taper portion 124. However, the present invention is not limited thereto. For example, as shown in FIG. 7, the outer taper portion 113' may be modified so as to be spaced away from the inner taper portion 124 to form a drain outlet 250 between a tip end of the outer taper portion 113' and the inner taper portion 124. In this arrangement, a part of the exhaust gas and water droplets introduced from the outer introduction hole 115 to the clearance 119 is discharged from the drain outlet 250 together with a part of the exhaust gas introduced in the clearance 119. Furthermore, since the distance t2 between the tip end of the outer taper portion 113 and the inner taper portion 124 is set smaller than the distance t1 between the circumferential portion 112 of the outer protector 110 and the circumferential portion 122 of the inner protector 120, the velocity of the discharged exhaust gas and water droplets is increased. Therefore, dischargability of water droplets through the drain outlet 250 can be enhanced.

In FIG. 7, a tip end of the inner taper portion 124 protrudes from the tip end of the outer taper portion 113'. However, both of the tip ends may be axially aligned with one another.

The above embodiments are described while mentioning a full-range air/fuel ratio sensor. However, the present invention is not limited thereto, but may be applied to protectors for use in oxygen sensors, $NO_x$ sensors, HC sensors, temperature sensors, etc.

This application is based on Japanese Patent Application No. JP 2006-298526 filed Nov. 2, 2006, incorporated herein by reference in its entirety.

Having described our invention as related to the present embodiments, it is our intention that the invention not be limited by any of the details of the description, unless otherwise specified, but rather be construed broadly within its spirit and scope as set out in the accompanying claims.

What is claimed is:

1. A gas sensor comprising:
   a detecting element, extending in an axial direction of the gas sensor, and having a detecting portion which is provided at a front end portion of the detecting element and adapted to detect a gas component contained in a gas-to-be-measured;
   a housing which encloses the detection element therein with the detection portion of the detection element projecting from a front end of the housing;
   an inner protector accommodating the detection portion of the detection element therein, the inner protector including a bottom portion having an exhaust hole, a circumferential portion having inner introduction holes for introducing the gas-to-be-measured into the interior of the inner protector, and a rear end portion fixed to a front end portion of the housing; and
   an outer protector enclosing the inner protector therein with a clearance present between the inner protector and the outer protector, the outer protector including a circumferential portion having outer introduction holes for introducing the gas-to-be-measured into the clearance, and a rear end portion fixed to the front end portion of the housing, wherein an axial distance h (mm) between a front end of the detection element and the exhaust hole and a diameter r (mm) of the exhaust hole satisfy a relation $r \leq 2h/15 + \frac{1}{3}$, where $0 < h$ and $0 < r$;

wherein the diameter r of the exhaust hole is equal to or greater than 0.5 mm; and wherein the axial distance h between the front end of the detection element and the exhaust hole is equal to or less than 15 mm.

2. The gas sensor according to claim 1, wherein the outer introduction holes are located frontward of the inner introduction holes of the inner protector with respect to the axial direction.

3. The gas sensor according to claim 1, comprising a protection layer of porous ceramic formed on a surface of a front end portion of the detection element and adapted to protect against adhesion of water, wherein the protection layer has a thickness of 150 μm to 250 μm at the front end of the detection element.

4. The gas sensor according to claim 1, wherein each of the inner protector and the outer protector has a taper portion at a front end portion thereof.

5. The gas sensor according or claim 4, comprising a water outlet provided between a tip end of the taper portion of the outer protector and the taper portion of the inner protector.

6. The gas sensor according to claim 5, wherein a clearance between the tip end of the taper portion of the outer protector and the taper portion of the inner protector is smaller than a clearance between the circumferential portion of the outer protector and the circumferential portion of the inner protector.

7. The gas sensor according to claim 1, wherein the bottom portion of the inner protector is exposed from the outer protector, and the diameter r of the exhaust hole is smaller than a diameter R of the inner introduction holes.

8. A gas sensor comprising:

a detecting element extending in an axial direction of the gas sensor and having a detecting portion which is provided at a front end portion of the detecting element and adapted to detect a gas component contained in a gas-to-be-measured;

a housing which encloses the detection element therein with the detection portion of the detection element projecting from a front end of the housing;

an inner protector accommodating the detection portion of the detection element therein, the inner protector including a bottom portion having an exhaust hole, a circumferential portion having inner introduction holes for introducing the gas-to-be-measured into the interior of the inner protector, a inner taper portion connecting the bottom portion and the circumferential portion, and a rear end portion fixed to a front end portion of the housing;

an outer protector enclosing the inner protector therein with a clearance present between the inner protector and the outer protector, the outer protector including a outer taper portion, a circumferential portion having outer introduction holes for introducing the gas-to-be-measured into the clearance, and a rear end portion fixed to the front end portion of the housing; and a drain outlet defined by a tip end of the outer taper portion of the outer protector and the inner taper portion of the inner protector;

wherein the outer introduction holes are disposed at a location closer to the front end of the housing than the inner introduction holes.

9. The gas sensor according to claim 8, wherein a clearance between a tip end of the taper portion of the outer protector and the taper portion of the inner protector is smaller than a clearance between the circumferential portion of the outer protector and the circumferential portion of the inner protector.

* * * * *